United States Patent
Franke et al.

(10) Patent No.: US 7,329,748 B2
(45) Date of Patent: Feb. 12, 2008

(54) METHOD FOR THE PRODUCTION OF RIBOFLAVIN OF MODIFICATION B/C IN GRANULAR FORM

(75) Inventors: Dirk Franke, Birkenheide (DE); Friedrich Hill, Meckenheim (DE); Christoph Martin, Mannheim (DE); Thomas Knebel, Schifferstadt (DE)

(73) Assignee: BASF Aktiengesellschaft (DE)

( * ) Notice: Subject to any disclaimer, the term of this patent is extended or adjusted under 35 U.S.C. 154(b) by 212 days.

(21) Appl. No.: 10/552,137

(22) PCT Filed: Apr. 7, 2004

(86) PCT No.: PCT/EP2004/003689

§ 371 (c)(1),
(2), (4) Date: Oct. 6, 2005

(87) PCT Pub. No.: WO2004/089889

PCT Pub. Date: Oct. 21, 2004

(65) Prior Publication Data

US 2006/0258664 A1    Nov. 16, 2006

(30) Foreign Application Priority Data

Apr. 11, 2003   (DE) ................................. 103 17 051

(51) Int. Cl.
*C07D 487/04*   (2006.01)

(52) U.S. Cl. ..................................................... 544/251

(58) Field of Classification Search ................. 544/251
See application file for complete search history.

(56) References Cited

U.S. PATENT DOCUMENTS 5,300,303 A    4/1994  Grimmer et al.
6,150,364 A    11/2000 Wagner

FOREIGN PATENT DOCUMENTS

| | | |
|---|---|---|
| CA | 2 306 502 | * 10/2000 |
| EA | 1 048 668 | 11/2000 |
| EP | 0 307 767 | 3/1989 |
| EP | 0 457 075 | 11/1991 |
| EP | 0 730 034 | 9/1996 |
| EP | 0 995 749 | 4/2000 |

* cited by examiner

*Primary Examiner*—Mark L. Berch
*Assistant Examiner*—Cecilia M Jaisle
(74) *Attorney, Agent, or Firm*—Connolly Bove Lodge & Hutz LLP

(57) ABSTRACT

The present invention relates to an improved process for preparing riboflavin of the B/C modification in granule form. Furthermore, the invention relates to the riboflavin preparation process wherein riboflavin of the A modification is (a) dissolved in aqueous mineral acid without treating the resulting riboflavin solution with activated carbon, (b) precipitated directly afterwards, steps (a) and (b) being carried out at a temperature in the range from 5 to 15° C., and (c) dried by fluidized bed granulation; and wherein the riboflavin does not come into contact with the aqueous mineral acid solvent for longer than on average 4 hours.

20 Claims, No Drawings

METHOD FOR THE PRODUCTION OF RIBOFLAVIN OF MODIFICATION B/C IN GRANULAR FORM

RELATED APPLICATIONS

This application is a national stage application (under 35 U.S.C. 371) of PCT/EP2004/003689 filed Apr. 7, 2004 which claims benefit to German application 103 17 051.0 filed Apr. 11, 2003.

The present invention relates to an improved process for preparing pure riboflavin (vitamin B2) of the B/C modification in granule form. In addition, the invention relates to pure riboflavin in granule form, which features particularly good dissolution at high bulk density.

When riboflavin (vitamin B2) is used which is intended as an active ingredient or additive for foods or pharmaceuticals, very high demands on the purity of the product have to be fulfilled. This constitutes one of the main requirements on the currently conducted synthetic or biotechnological processes for industrially preparing riboflavin.

In general, riboflavin prepared by biotechnological processes occurs in an initial purity of about 75%, which is attributed mainly to impurities which are typical of biotechnological preparative processes, for instance cell residues, proteins, peptides or else amino acids. Such crude products are therefore unsuitable for the aforementioned applications in humans and require further purification.

For some time, there has existed a need for an economic process which enables highly pure riboflavin having satisfactory solubility properties to be prepared. The main emphasis is on processes for preparing riboflavin in the B and/or C modifications, especially riboflavin which is substantially in the B modification and may comprise small amounts of riboflavin of the C modification, which is difficult to detect (referred to hereinbelow as riboflavin of the B/C modification).

A first approach to this aim is described by EP-A 0 307 767: to prepare a spherulitic form of riboflavin having improved handling and flow properties, riboflavin is dissolved in a solvent and is precipitated using a second solvent in which riboflavin is insoluble but which is miscible with the first solvent.

EP-A 0 457 075 describes a process for preparing very free-flowing, nondusting and binder-free riboflavin spray granules or microgranules from pure riboflavin. In this process, an aqueous or water-containing suspension of pure, finely divided riboflavin is subjected to spray fluidized bed drying, to single-material nozzle atomization drying or to disk atomization drying.

EP-A 0 995 749 describes a purification and crystallization process for riboflavin. In this process, riboflavin of the A modification is dissolved in aqueous mineral acid and purified by admixing with activated carbon. After a filtration, the material of value is precipitated by adding water in the method described by EP-A 0 307 767 and isolated. This gives dendritic spherical crystals of the B/C modification.

EP-A 1 048 668 describes a process which is based on the teaching of EP-A 0 457 075 and prepares nondusting and binder-free riboflavin granules having good flow properties. In this process, the riboflavin, as described in EP-A 0 995 749, is initially purified by activated carbon and, after a subsequent crossflow filtration, precipitated at a temperature of from 0 to 30° C. Afterwards, the aqueous riboflavin suspension obtained in this way is filtered and washed, and the riboflavin of the B/C modification isolated in this way is subjected to spray fluidized bed drying, to single-material nozzle atomization drying or to disk atomization drying.

Granules, as described, for example, in EP-A 1 048 668, are generally notable for good solubility properties, but have a low bulk density, which considerably complicates their handling and further processing.

There is therefore still a need for a process for preparing pure riboflavin which, in combination with good dissolution kinetics which are sufficient for pharmacological and food technology applications, has generally good handling properties and in particular a high bulk density.

A process has now been found for preparing riboflavin of the B/C modification in granule form, which comprises a) dissolving riboflavin of the A modification in aqueous mineral acid, b) directly afterwards, without initially treating the resulting riboflavin solution in mineral acid with activated carbon, precipitating, steps a) and b) being carried out at a temperature in the range from 5 to 15° C., and c) drying the riboflavin by fluidized bed spray granulation.

The riboflavin granules prepared in this way are notable for particularly advantageous dissolution kinetics and a high bulk density. The properties of the granules are such that they can be dissolved rapidly in aqueous media even after pressing to tablet form (tableting), in spite of their high density.

In addition to the low dissolution temperature of the preparative process according to the invention, this particularly advantageous combination of properties also depends upon how long the riboflavin comes into contact with the mineral acid medium used as a solvent. A shortening of the contact time leads to an improvement in the inventive product properties. The shortening of the contact time of riboflavin and mineral acid medium is achieved in the process according to the invention, among other measures, by omitting the time-consuming purification step of adding activated carbon, and carrying out the precipitation immediately after the dissolution procedure. In this context, immediately means that no further process steps or prolonged lifetimes of the solution are envisaged between dissolution procedure and precipitation which go beyond the necessary transport of the solution from the dissolution tank to the first precipitation tank, for example through pipelines. Nor is it necessary to use other adsorbents familiar per se to those skilled in the art.

The limiting of the contact time of the riboflavin with the mineral acid dissolution medium results in the decomposition products which are always formed in traces on treatment with acid being generated to a relatively slight extent, which, after precipitation and final fluidized bed spray granulation, leads to the particularly advantageous properties of the inventively prepared granular riboflavin. It is thus the combination of the process features illustrated which leads to the advantageous properties of the riboflavin granules according to the invention.

The process according to the invention is suitable for preparing pure riboflavin of the B/C modification in granule form. The starting substance used is riboflavin which has been prepared synthetically or by fermentation, but preferably by fermentation, and, after the preparation, has optionally already passed through at least one purification step, for example by reprecipitation, and has a purity which is typically in the range from 90 to 99%. A preferred starting material is riboflavin having a purity of from 95 to 99%, more preferably having a purity of from 97 to 99%. This is typically completely or predominantly (i.e. more than about 90%) present in the A modification, but can in principle be used in any desired modification.

According to the invention, the riboflavin serving as a starting substance is dissolved in aqueous mineral acid, for example in nitric acid or, preferably, in hydrochloric acid. The concentration of the mineral acid is typically from about 10 to about 65% by weight. The aqueous hydrochloric acid preferably used as the dissolution medium appropriately has a concentration in the range from about 18 to about 28% (% by weight).

The dissolution procedure in the process according to the invention is effected at a temperature of the dissolution medium in the range from about 5° C. to about 15° C. Preference is given to dissolution temperatures in the range from 5° C. to 12° C., most preferably from 6° C. to 9° C. This gives solutions in which up to about 20% by weight riboflavin is dissolved. In general, the dissolution procedure is complete after from 30 to 150 min.

The duration of the dissolution procedure is selected in such a way that the overall time during which the riboflavin is in contact with the mineral acid solvent is very short. In this context, the overall contact time is the time from the beginning of the dissolution procedure until precipitation of the riboflavin from the aqueous hydrochloric acid dissolution medium, i.e. the time during which the riboflavin is dissolved in the aqueous hydrochloric acid dissolution medium. It is advantageous to work with overall contact times up to about 4 h. Particular preference is given to overall contact times from about 2.5 to about 3 h. Since the process according to the invention preferably also includes continuous process steps, the contact times specified, like all further time data (for example dissolution or precipitation time), are to be interpreted as average times.

For precipitation, the mineral acid riboflavin solution is admixed with water, typically with from about five to ten times the amount (v/v). In the case of aqueous hydrochloric acid, which is preferably used as a solvent in accordance with the invention, preference is given to adding sufficient water to obtain a hydrochloric acid concentration of from about 1.5 to about 4% by weight, preferably from about 2 to about 3% by weight.

The riboflavin can be precipitated continuously or batchwise in one or more stirred tanks connected in series, known as a stirred tank battery. In a preferred embodiment of the process according to the invention, the precipitation is carried out continuously in a two-stage stirred tank battery.

According to the invention, the temperature in the course of the precipitation is selected in such a way that it is within the range from about 5° C. to about 15° C., in particular from about 6° C. to about 12° C. Particular preference is given to a precipitation temperature in the range from about 7° C. to about 10° C.

The average residence times of the riboflavin solution in the inventively preferred, continuous precipitation of the riboflavin in the first stirred tank are in the range from about 1 min to about 10 min, preferably from about 2.5 min to about 5 min. The residence time in the second tank can vary more widely, but is appropriately selected within the range from about 5 to about 15 min, preferably from about 5 min to about 10 min.

The stirrer output in the first tank and, independently thereof, in the second tank too, is advantageously from about 0.02 W/l to about 1.0 W/l. Preference is given to selecting, independently for each tank, a stirrer output in the range from about 0.05 to about 0.3 W/l.

The riboflavin which can be prepared by the process steps according to the invention is in the form of agglomerates. These have a high density and a smooth surface and feature, in particular with regard to the further processing which is typically also necessary, considerable advantages compared to conventional spherical riboflavin crystals. The conventional crystals sometimes have a spiny surface (see EP-A 0 995 749) and have low shear stability. This property, which is unfavorable for the process control, promotes the growth of needle-shaped crystals and leads, inter alia, to poor process stability and to poor filtration and handling properties.

The process control of the precipitation can be used to influence the agglomerate formation. In the case of continuous operation with two tanks, care has to be taken that the feed streams are metered precisely. The mixing times should be short, in order to prevent localized overconcentrations. The latter can be achieved by suitable choice of the stirrer and also of the metering points, as familiar to those skilled in the art. It may possibly be advantageous to divide the feed of water and riboflavin solution to the vessels. However, not more than 70% of the water should be added to the second reactor. A further possibility for concentration adjustment is offered by the recycling of suspension from the second precipitation vessel, and also the recycling of mother liquor after the filtration. This means that the solids concentration can be freely selected, which influences the agglomeration kinetics. When the suspensions are removed from the reactor, it is to be noted that this can also result in changes in the solids concentration in the reactor. This can also result in changes in the agglomeration kinetics. The particle size of the agglomerates changes as a function of the dispersion in the pipelines, which likewise influences the available surface area.

In order to ensure full conversion, it may be prudent to provide further residence time downstream of the second stirred tank. The latter may be realized in the form of a stirred tank.

The advantageous version of the precipitation step may differ between pilot plant and operation scale. When the process according to the invention is carried out on the industrial scale, the product properties which are advantageous compared to the prior art arise particularly distinctly when the process steps connected in series are in a steady state. This state is attained typically after about 10 cycles. In the process carried out on a smaller scale, for example on the laboratory or pilot plant scale, it may be possible and advantageous to further reduce the overall contact time of the riboflavin with the aqueous mineral acid dissolution medium.

Afterwards, the precipitated riboflavin is removed from the aqueous precipitation medium by filtration methods which are familiar per se to those skilled in the art, and washed.

The filtercake obtainable by the filtration, consisting of solid riboflavin of the B/C modification, is advantageously suspended by adding water. The amount of the water added is selected in such a way that a riboflavin suspension having a solids content of from about 5 to about 15% by weight, preferably from about 8 to about 12% by weight, is obtained. However, it is also possible to use a suspension in a solvent having not too high a boiling point when this solvent comprises water. The water content in the suspension should then be at least 10% by weight. Useful solvents are in particular water-miscible solvents, for example $C_1$- to $C_4$-alkanols.

For drying, the riboflavin suspension is subjected to a fluidized bed spray granulation. In contrast to the known spray drying of riboflavin solutions or suspensions, in which they are typically sprayed into the drying tower by means of a two-material nozzle, the suspension in the fluidized bed spray granulation employed in accordance with the invention is sprayed continuously or batchwise into a fluidized bed of dry reaction product. The drying unit is provided with apparatus which allows a certain particle size fraction to be obtained and the granulation process to be maintained (cf. K. Kroll, Trocknungstechnik [drying technology], Volume II, "Trockner und Trocknungsverfahren" ["dryers and drying processes"], Springer, Berlin, 1978, 221-223).

It is advantageous to work in a continuous spray fluidized bed (cf. H. Uhlemann, "Wirbelschichtsprühgranulation" ["fluidized bed spray granulation"], Springer, 2000, 219-244) with integrated filter and a nozzle arrangement which allows the riboflavin suspension to be sprayed from above onto or into the fluidized bed (known as the "top-spray process").

To carry out the fluidized bed spray granulation according to the invention, the procedure is generally to a) initially charge riboflavin in the form of a dry powder or of spray or microgranules in a fluidized bed dryer, in a fluidized bed heated to from 20 to 100° C., preferably from 50 to 100° C., in particular from 65 to 95° C.,
b) add to this an aqueous or water-containing suspension of the finely divided riboflavin in sprayed form as a function of the drying rate,
c) remove the riboflavin particles from the fluidized bed after a suitable residence time and separate them into particle fractions using a suitable apparatus,
d) discharge the particle fraction in the particle size range from about 50 to about 450 μm, preferably from about 80 to about 250 μm and
e) recycle the more finely divided particles and/or the more finely divided particles obtained by grinding larger particles and/or a portion of the fraction discharged as the useful fraction with or without grinding into the spray fluidized bed.

The spray fluidized bed drying can be carried out continuously or batchwise. It is particularly advantageous to work continuously.

To carry out the process, a riboflavin product first has to be prepared from the dry riboflavin powder corresponding to the prior art which is suitable for generating a fluidized bed. In the batchwise procedure, a sufficiently finely divided product, as obtained, for example, by spray drying or agglomerating spray drying, can be initially charged in the fluidized bed. Depending on the residence time of the particles in the spray fluidized bed, a dry product is then obtained which has a smaller or larger particle size range. Particles in the size range from about 50 to 450 μm have the desired properties and are therefore obtained as the product of value. Smaller particles, and also riboflavin obtained by grinding larger particles, are used as fluidized bed material for further batches.

To carry out the continuous process, the aqueous or water-containing suspension of finely divided riboflavin is sprayed continuously into a fluidized bed. The rate of the spray introduction is set in such a way that the fluidized bed has a temperature corresponding to the desired degree of drying. The temperature is determined by the difference between inlet and outlet temperature of the fluidizing gas blown into the dryer.

In continuous process control, when the fluidized bed dryer is started up for the first time, the starting material in the fluidized bed is finely divided riboflavin. Afterwards, a dry product is obtained which has virtually constant particle size distribution. From this it is advantageous to remove, continuously or intermittently, a certain portion of the desired particle size fractions. The particle fraction in the particle size range from about 50 to about 450 μm is discharged as a product of value and the finely divided particles and/or the finely divided particles obtained by grinding larger particles are recycled continuously into the fluidized bed to maintain the granulation process.

To attain the desired product properties, it may be advantageous likewise to grind a portion of the useful fraction removed and recycle it into the process. It is particularly advantageous to select the ratio of the stream recycled into the spray fluidized bed to the stream which is removed from the process as the product of value within the range from about 0 to about 8, preferably from about 0.5 to about 5, more preferably from about 1 to about 4.

The amount of riboflavin corresponding to the amount removed as the product of value is sprayed into the fluidized bed continuously in the form of an aqueous suspension of finely divided riboflavin, thus keeping the amount of riboflavin in the fluidized bed constant.

The fluidizing gas blown into the dryer to form the fluidized bed generally has an inlet temperature from 60 to 250° C., preferably from 140 to 185° C., and an outlet temperature from 40 to 140° C., preferably from 60 to 95° C. This results in a fluidized bed temperature of from about 40 to 140° C., preferably from 60 to 95° C., more preferably from 65 to 95° C.

The evaporation of the amount of liquid introduced into the fluidized bed with the aqueous riboflavin suspension can require the supply of additional energy. To this end, for example, heating surfaces can be immersed in the fluidized bed. The temperature of the heating surfaces is typically in the range from 100 to 250° C., preferably in the range from 140 to 180° C.

In a particularly preferred embodiment of the process according to the invention, a dryer is used which is configured in such a way that the spray nozzle or spray nozzles is or are arranged above the fluidized bed, in what is known as the top-spray configuration. The spray introduction procedure is controlled in such a way that the ratio of nozzle air to suspension introduced by spraying, based on the masses, is less than about 1.5, preferably less than about 1.

The process described is suitable for preparing pure riboflavin of the B/C modification in granule form. In this context, pure riboflavin is riboflavin which has a degree of purity of more than 96%, preferably of more than 98%, more preferably of more than 99%, and has not been admixed with binding or granulating auxiliaries or other additives.

The invention further relates to pure riboflavin in granule form which has a bulk density of from 0.45 to 0.7 g/ml and, after tableting, has a dissolution of at least 80%. The invention preferably relates to pure riboflavin in granule form which has a bulk density of from 0.5 to 0.65 g/ml and, after tableting, has a dissolution of at least 80%. The invention more preferably relates to pure riboflavin in granule form which has a bulk density of from 0.5 to 0.65 g/ml and, after tableting, has a dissolution of at least 85%.

In this context, bulk density is the quotient of the mass and the volume which is taken up by a material which can assume shape (in this case riboflavin in granule form) and is poured in a certain manner.

The determination of the bulk density of the riboflavin according to the invention in granule form, and also riboflavin products or administration forms of riboflavin which have been obtained in a different way and are to be compared thereto, is to be carried out in accordance with DIN 53468 (November 1960).

The bulk density of a water-soluble bulk material typically correlates with the dissolution kinetics, i.e. with the rate at which the bulk material dissolves in water or an aqueous dissolution medium, in such a way that those skilled in the art can expect a decreased dissolution rate from an increased bulk density.

Surprisingly, the inventive riboflavin in granule form, even after tableting, i.e. after compression to tablet form, exhibits surprisingly good dissolution kinetics.

To tablet the inventive riboflavin in granule form, and also riboflavin products which have been obtained in other ways and are to be compared thereto, a powder mixture consisting of 16.66% by weight of riboflavin, 53.34% by weight of Tablettose (Meggle AG), 26.84% by weight of Avicel® PH 102 (FMC Corp.), 0.5% by weight of Ac-Di-Sol® (FMC Corp.), 2.0% by weight of Aerosil® 200 (Degussa AG) and 0.66% by weight of magnesium stearate (Bärlocher GmbH) is initially prepared. To this end, all the ingredients, with the exception of the riboflavin and also of the magnesium stearate, are intimately mixed for 10 min in a Turbula mixer and subjected to forced sieving through a sieve of mesh width 0.8 mm, the riboflavin and the magnesium stearate are added, and the mixture is mixed in the Turbula mixer for another 10 min. The powder mixture prepared in this way is compressed with a Korsch PH 106 tablet press at a tableting rate of 20 revolutions/min and a compressive-force of 10 kN to give beveled, biplanar tablets having a diameter of 8 mm, a weight of 300 mg and a riboflavin content of 50 mg.

A suitable measure for determining the dissolution kinetics of the riboflavin granules according to the invention after the tableting carried out as described above is the dissolution.

To determine the dissolution of the tableted riboflavin, a fully automatic release instrument according to U.S.P. 26 (Physical Tests/711 Dissolution, p. 2155) is used. The measurement is carried out in a 1 liter measuring cylinder which is filled with 900 ml of 0.1 molar hydrochloric acid. The measurement solution is heated in a water bath to from 36.5 to 37.5° C. and stirred with a paddle stirrer at 75 revolutions/min. 30 minutes after addition of the riboflavin tablet prepared as described above, a sample of the measurement solution is taken whose riboflavin content, optionally after further dilution, is determined by UV spectroscopy at a wavelength of 267 nm. The proportion of the amount of riboflavin released from the tablet after 30 min is reported in [%] as the dissolution.

The combination of the properties mentioned, which has hitherto not been achieved, makes the inventive riboflavin granules superior to the administration forms of riboflavin known hitherto. At the same time, the inventive granules are very free-flowing, nondusting and binder-free. They are preferably obtained without adding granulating auxiliaries.

The following examples serve to illustrate the process according to the invention, but without limiting it:

EXAMPLES

Example 1

General Method for Preparing Riboflavin in Granule Form 100 kg of an aqueous solution which has been prepared at the dissolution temperature X (see Table 1) and comprises 10% by weight of riboflavin and 22% by weight of HCl are introduced continuously into a stirred tank at a rate of 48 kg/h together with 360 l/h of water. The solution remains there at a temperature of 8° C. and an introduced stirrer output of approx. 0.12 W/l at an average residence time of 4:30 min for precipitation. After a further residence time of approx. 6 min in a downstream stirred tank, the resulting suspension is filtered through a belt filter and the residue is washed with water. In this way, an overall contact time of the riboflavin with the hydrochloric acid dissolution medium of about 2:30 h is attained.

An aqueous suspension which comprises about 10% by weight of this residue is sprayed from above onto the fluidized initial charge of a fluidized bed dryer at a rate of 4 kg/h and an air feed temperature of 180° C. by means of a two-material nozzle. During the experiment, granules are removed from the product chamber, so that the contents of the fluidized bed remain constant. The effluent is fractionated with a sieve (250 μm). The coarse material is comminuted using a universal mill and reintroduced to the fluidized bed, the ratio of recycled to discharged product being 1:1.

TABLE 1

| Experiment | Dissolution temperature X [° C.] | Dissolution [%] | Bulk density [g/ml] |
|---|---|---|---|
| Experiment 1 | 12 | 86 | 0.57 |
| Experiment 2 | 8 | 89 | 0.57 |
| Comparative experiment 1 | 3 | —/—* | —/—* |
| Comparative experiment 2 | 22 | 78 | 0.61 |

*strongly dusting product which could not be granulated

Example 2

Drying of Riboflavin Suspensions Prepared According to Example 1 on the Industrial Scale The spray granulation is effected in a fluidized bed apparatus having an incident flow surface area of 0.07 m². The flow rate of the suspension sprayed in is between about 12 and 20 kg/h. The product chamber of the fluidized bed apparatus is provided with heating surfaces heated to 160° C. The fluidization gas is blown in at a temperature of 166° C. For particle size control, a portion of the fluidized material is removed and separated with a sieve machine into two fractions (useful fraction <250 μm, coarse fraction >250 μm). The coarse fraction and, if required, a portion of the useful fraction, are ground and recycled into the fluidized bed. The ratio of recycled to discharged product is given by the values under "recycling" in Table 2.

TABLE 2

| Experiment | Recycling | Dissolution [%] | Bulk density [g/ml] |
|---|---|---|---|
| Experiment 3 | 1:1 | 83 | 0.56 |
| Experiment 4 | 2.1:1 | 88 | 0.54 |

Example 3

Bulk Densities and Dissolution Values of Riboflavin Granules

TABLE 3

| Sample | Dissolution [%] | Bulk density [g/ml] |
|---|---|---|
| Riboflavin Tablet Grade (F. Hoffmann-La Roche AG) | 78 | 0.388 |
| Inventive riboflavin in granule form | 90 | 0.501 |
| Riboflavin High Flow 95 (Takeda Ltd.) | 85 | 0.385 |
| Riboflavin 100 (BASF Aktiengesellschaft) | 73-75 | 0.350 |

We claim:

1. A process for preparing riboflavin of the B/C modification in granule form, wherein riboflavin of the A modification
   a) is dissolved in aqueous mineral acid without activated carbon,
   b) is precipitated directly afterwards, steps a) and b) being carried out at a temperature in the range from 5 to 15° C., and
   c) the riboflavin is dried by fluidized bed spray granulation, and wherein the riboflavin does not come into contact with the aqueous mineral acid solvent for longer than on average 4 h.

2. The process according to claim 1, wherein the dissolution temperature is selected within the range from 5 to 12° C.

3. The process according to claim 1, wherein the riboflavin does not come into contact with the aqueous mineral acid solvent for longer than on average 3 h.

4. The process according to claim 1, wherein the precipitation is carried out within a temperature range from 6 to 12° C.

5. The process according to claim 1, wherein the precipitation is carried out continuously.

6. The process according to claim 1, wherein the precipitation is carried out in a two-stage stirred tank battery.

7. The process according to claim 1, wherein the precipitation is carried out in the first stirred tank of the two-stage stirred tank battery with an average residence time of the riboflavin solution in the first stirred tank of from 1 to 10 min.

8. The process according to claim 1, wherein drying is carried out using a continuous or semicontinuous fluidized bed spray granulation in top-spray configuration.

9. The process according to claim 1, wherein the temperature of the dry gas blown into the dryer in the fluidized bed spray granulation is in the range from 100 to 200° C.

10. The process according to claim 1, wherein the temperature of the dry gas blown into the dryer in the fluidized bed spray granulation is in the range from 150 to 170° C.

11. The process according to claim 1, wherein a portion of the ribofla-vin obtained after the drying is recycled back into the drying process, and the ratio of the stream recycled into the spray fluidized bed to the stream which is removed from the process as the product of value is from about 1:1 to about 4:1.

12. The process according to claim 2, wherein the riboflavin does not come into contact with the aqueous mineral acid solvent for longer than on average 3 h.

13. The process according to claim 3, wherein the precipitation is carried out within a temperature range from 6 to 12° C.

14. The process according to claim 4, wherein the precipitation is carried out continuously.

15. The process according to claim 5, wherein the precipitation is carried out in a two-stage stirred tank battery.

16. The process according to claim 6, wherein the precipitation is carried out in the first stirred tank of the two-stage stirred tank battery with an average residence time of the riboflavin solution in the first stirred tank of from 1 to 10 min.

17. The process according to claim 7, wherein drying is carried out using a continuous or semicontinuous fluidized bed spray granulation in top-spray configuration.

18. The process according to claim 8, wherein the temperature of the dry gas blown into the dryer in the fluidized bed spray granulation is in the range from 100 to 200° C.

19. The process according to claim 9, wherein the temperature of the dry gas blown into the dryer in the fluidized bed spray granulation is in the range from 150 to 170° C.

20. The process according to claim 10, wherein a portion of the riboflavin obtained after the drying is recycled back into the drying process, and the ratio of the stream recycled into the spray fluidized bed to the stream which is removed from the process as the product of value is from about 1:1 to about 4:1.

* * * * *